United States Patent [19]
Garst et al.

[11] Patent Number: 5,258,400
[45] Date of Patent: Nov. 2, 1993

[54] ANTI-INFLAMMATORY FURANONE COMPOUNDS

[75] Inventors: Michael E. Garst, Newport Beach; Elizabeth T. Syage, Cypress, both of Calif.

[73] Assignee: Allergan, Inc., Irvine, Calif.

[21] Appl. No.: 872,776

[22] Filed: Apr. 23, 1992

Related U.S. Application Data

[60] Division of Ser. No. 709,550, Jun. 3, 1991, Pat. No. 5,112,853, which is a continuation of Ser. No. 439,733, Nov. 20, 1989, abandoned.

[51] Int. Cl.$^5$ ................... A61K 31/38; C07D 333/54
[52] U.S. Cl. ................... 514/443; 514/444; 514/473; 549/58; 549/318; 549/320
[58] Field of Search ............... 514/443, 444, 473; 549/58, 318, 320

[56] References Cited

U.S. PATENT DOCUMENTS

| | | | |
|---|---|---|---|
| 2,359,096 | 9/1944 | Elderfield | 260/239.5 |
| 2,359,208 | 9/1944 | Elderfield | 260/344 |
| 4,447,445 | 5/1984 | Jacobs | 424/279 |
| 4,786,651 | 11/1988 | Wheeler | 514/460 |
| 4,789,749 | 12/1988 | Jacobs et al. | 549/313 |
| 4,855,320 | 8/1989 | Chatterjee et al. | 514/473 |
| 4,874,782 | 10/1989 | Bonjouklian et al. | 514/473 |
| 4,916,241 | 4/1990 | Hayward et al. | 549/313 |
| 4,935,530 | 6/1990 | Lee | 549/214 |
| 5,013,850 | 5/1991 | Lee | 549/222 |
| 5,037,811 | 8/1991 | Lee | 514/99 |
| 5,043,457 | 8/1991 | Lee | 549/222 |
| 5,045,564 | 9/1991 | Lee | 514/471 |
| 5,059,611 | 10/1991 | Lee | 514/336 |
| 5,081,147 | 1/1992 | Lee | 514/471 |
| 5,081,261 | 1/1992 | Lee | 549/222 |
| 5,082,954 | 1/1992 | Lee | 549/214 |
| 5,089,485 | 2/1992 | Lee | 514/99 |
| 5,112,853 | 5/1992 | Garst | 514/443 |

FOREIGN PATENT DOCUMENTS

| | | |
|---|---|---|
| 133376 | 2/1985 | European Pat. Off. . |
| 209274 | 1/1987 | European Pat. Off. . |
| 295056 | 6/1987 | European Pat. Off. . |
| 350878 | 1/1990 | European Pat. Off. . |

OTHER PUBLICATIONS

Bonjuklian, et al., Chemical Abstracts, vol. 106, 156260c, p. 670 (19987).
Reynolds, et al, J. Am. Chem. Soc., 110, pp. 5172–5177 (1988).
Tocanne et al., Chemical Abstracts 69 76581k, p. 7146 (1968).
Deems, et al, Biochimica et Biophysica Acta, 917 pp. 258–268 (1987).
Scheuer et al., Journal of the American Chemical Society 100:1 p. 307 (Jan. 4, 1978).
Graziano, et al., Chemical Abstracts 107, (1987), 236559t.
Roll et al., Org. Chem. (1988), 53 3276-8.
Negishi et al., J. Org. Chem 45, pp. 5223–5225, (1980).
E. D. de Silva et al., "Tetrahedron Letters", 21:1611–1614 (1980).
Nakagawa et al., "Aldose reductase inhibitor from Palaun sponges" Chem. Abstract 106: 96126b, 1987.
Tanaka, et al., The Chemical Society of Japan, Chemistry Letters, pp. 633–636 (1983).
Tanis, et al., Tetrahedron Letters, vol. 25, No. 40, pp. 4451–4454 (1984)–Furans in Synthesis 4. Silyl Furans as Butenolide Equivalents.

*Primary Examiner*—C. Warren Ivy
*Assistant Examiner*—Ba K. Trinh
*Attorney, Agent, or Firm*—Gabor L. Szekeres; Martin A. Voet; Robert J. Baran

[57] ABSTRACT

New furanone compounds have anti-inflammatory, immunosuppresive and anti-proliferative activity and are useful in treating psoriasis and modifying calcium homeostasis. A compound of the invention is 4-[3,6-dihydro-6-hydroxy-5-(3-phenylpropyl)-2H-pyran-2-yl]-5-hydroxy-2-(5H)-furanone.

3 Claims, No Drawings

ANTI-INFLAMMATORY FURANONE COMPOUNDS

CROSS-REFERENCE TO RELATED APPLICATION

The present application is a divisional of application Ser. No. 07/709,550 filed on Jun. 3, 1991, now U.S. Pat. No. 5,112,853, which in turn was a continuation of application Ser. No. 07/439,733 filed on Nov. 20, 1989, now abandoned.

This invention relates to new furanone compounds having anti-inflammatory activity, pharmaceutical compositions comprising these compounds and to methods of using them.

BACKGROUND OF THE INVENTION

Manoalide is a furanone compound isolated from marine sponge as reported by E. D. de Silva et al., *Tetrahedron Letters* 1611–1614 (1980). Anti-inflammatory, immunosuppresive and analgesic properties of manoalide are disclosed in U.S. Pat. No. 4,447,445. Manoalide has the following structural formula:

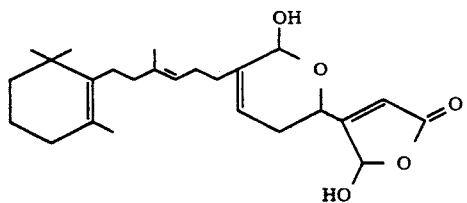

The anti-inflammatory activity of seco-manoalide and dehydro-seco-manoalide is also disclosed in U.S. Pat. No. 4,447,445.

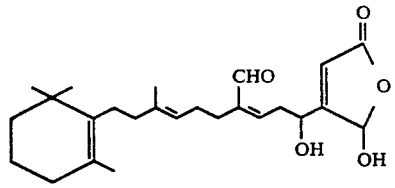

seco-manoalide

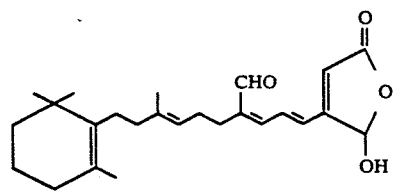

dehydro-seco-manoalide

THE INVENTION

The pyranyl furanone compounds of the present invention are represented by the following formula:

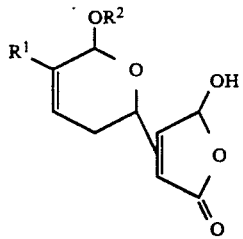

FORMULA I in which:
$R_1$ is $C_1$–$C_{17}$ alkyl or alkenyl having 1–5 unconjugated double bonds, phenyl($C_1$–$C_{17}$ alkyl or alkenyl having 1–5 unconjugated double bonds), benzothienyl ($C_1$–$C_{17}$ alkyl or alkenyl having 1–5 unconjugated double bonds), naphthyl ($C_1$–$C_{17}$ alkyl or alkenyl having 1–5 unconjugated double bonds), ($C_1$–$C_{17}$ alkyl, alkenyl having 1–5 unconjugated double bonds) and
$R_2$ is hydrogen or $C_1$–$C_4$ alkyl.

The phenyl rings in the definition of $R_1$ may be optionally substituted by standard substituents such as lower alkyl, lower alkoxy or halo, in particular, bromo or chloro.

Particular compounds of this invention represented by Formula I are those in which:
$R_1$ is phenyl($C_1$–$C_{17}$ alkyl) or benzothienyl ($C_1$–$C_{17}$ alkyl); and
$R_2$ is hydrogen.

Preferably the pyranyl ring is attached to the 4-position of the 2-furanone ring.

Preferred compounds of this invention are 4-[3,6-dihydro-6-hydroxy-5-(3-phenylpropyl)-2H-pyran-2-yl]-5-hydroxy-2(5H)-furanone. and 4-[5-(6-(benzo[b]thien-2-yl)-hexyl)-3,6-dihydro-6-hydroxy-2H-pyran-2-yl]-5-hydroxy-2(5H)-furanone.

Other compounds of this invention are represented by Formulas II, III and IV:

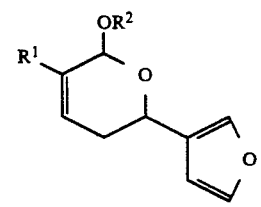

Formula II

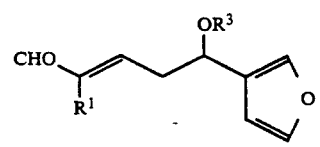

Formula III

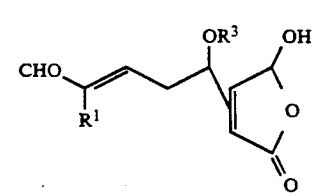

Formula IV

The terms $R_1$ and $R_2$ are as defined in Formula I and $R_3$ is hydrogen or $C_1$–$C_{12}$ alkanoyl, preferably acetyl.

The compounds of Formulas I and III and of Formula IV where $R_3$ is hydrogen are intermediates in the preparation of the anti-inflammatory compounds of Formula I. Also, the compounds of Formula IV have pharmacological activity similar to that demonstrated by the compounds of Formula I.

Certain of the compounds of this invention contain chiral centers and accordingly, may be prepared as enantiomeric or diasteriomeric mixtures or in optically pure form. Unless otherwise specified herein, the preparations are racemates at each chiral center. However, the scope of the invention is not to be considered as limited to these forms but also to encompass the individual optical isomers of the compounds.

Compounds of the invention are prepared by the following procedures:

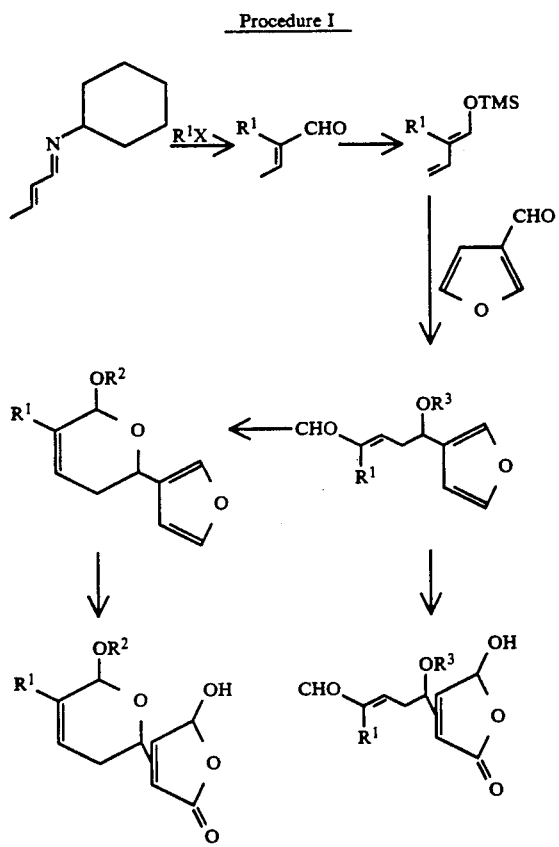

The term $R_1$ is as defined in Formula I, X is halo and TMS is trimethylsilyl.

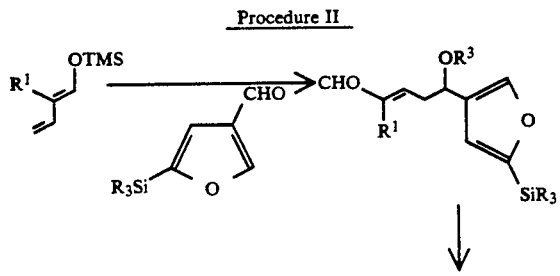

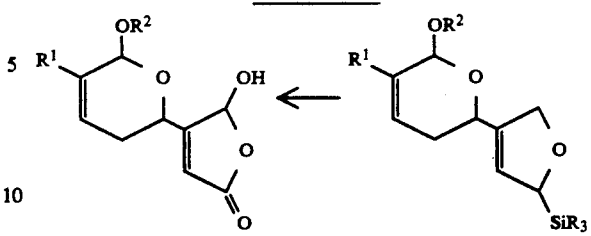

The term $R_1$ is as defined in Formula I and R is methyl or ethyl.

The compounds in which $R_2$ is $C_1$–$C_4$ alkyl are prepared by acetal exchange, using, for example, an alcohol and the compounds in which $R_3$ is $C_1$–$C_4$ alkanoyl are prepared by O-alkanoylating using an alkanoyl anhydride or halide by standard procedures as described in the examples. The alkylation and alkanoylation are conveniently carried out on the furan intermediates before oxidation to the hydroxyfuranone compounds.

According to Procedure I, a halide (RX) is reacted with crotonaldehyde cyclohexylimine. The resulting 2-$R_1$-2-butenal is reacted with trimethylsilyl chloride and the resulting 2-$R_1$-1-trimethylsilyloxy-1,3-butadiene is reacted with 3-furaldehyde to give the 5-furyl-5-hydroxy-2-$R_1$-2-pentenal. Treatment with ultraviolet light gives the 2-furyl pyran. Oxidation by treating with oxygen and irradiating using an initiator such as Rose Bengal gives the substituted pyranyl 5-hydroxy-2(5H)-furanone.

Alternatively, the 5-furyl-5-hydroxy-2-$R_1$-2-pentanal is treated with oxygen and irradiated using an initiator such as Rose Bengal to give the 5-(5-hydroxy-2(5H)-furanonyl)pentenal.

According to Procedure II, 2-$R_1$- 1-trimethylsilyloxy-1,3-butadiene is reacted with 5-trialkylsilyl-3-furaldehyde to give the 5-hydroxy-S-(2-trimethylsilyl-fur-4-yl)-2-$R_1$-2-pentenal. Treatment with ultraviolet light gives the 3,6-dihydro-2-(5-trialkylsilyl-3-furyl)-6-hydroxy-5-$R_1$-2H-pyran which on treatment with oxygen and irradiation using an initiator such as Rose Bengal gives the pyranyl furanone.

The 5-trimethylsilyl-3-furaldehyde starting material may be prepared by brominating 3-furaldehyde to give 5-bromo-3-furaldehyde which is converted to the dimethylacetal, then treated with t-butyl lithium and trimethylsilyl chloride.

A preferred method for preparing 5-trialkylsilyl-3-furaldehyde is by reacting lithium morpholide with 3-furaldehyde to protect the aldehyde group, then reacting with sec-butyl lithium and trialkylsilyl chloride to give 5-trialkylsilyl-3-furaldehyde.

In addition, this invention relates to pharmaceutical compositions containing the compounds of Formula I or of Formula IV as active ingredients and to methods of using the compounds and pharmaceutical compositions of this invention to produce anti-inflammatory, immunosuppressant and anti-proliferative activity. These compounds are useful in treating inflammation, in suppressing unwanted immune responses and in retarding proliferation of cells. Uses include treatment of rheumatoid arthritis, osteoarthritis, rheumatic carditis and autoimmune diseases such as allergic diseases, bronchial asthma and myasthenia gravis and ocular and dermal inflammatory diseases. The compounds are useful in treating psoriasis, acne, atopic diseases and allergic conjunctivitis. They are also useful as adjuvant therapy associated with organ and tissue transplants.

The activity of these compounds is demonstrated by inhibition of the enzyme phospholipase $A_2$ in vitro and by reduction of inflammation in the mouse ear anti-inflammatory assay in vivo.

Activity of compounds of this invention may also be demonstrated by inhibition of phosphoinositide-specific phospholipase C. This activity has been reported for manoalide and may indicate anti-inflammatory utility. Bennett et al, *Molecular Pharmacology* 32:587-593 (1987).

Activity of the compounds may also be demonstrated by inhibition of ornithine decarboxylase, a rate limiting enzyme in cellular growth, which indicates use in treating psoriasis and neoplasis.

The compounds also modify calcium homeostasis. This activity is shown by effect on intracellular calcium levels in experiments using gastric glands, spleen cells, epithelial cells, $GH_3$ cells, etc. Calcium is inhibited from entering through the plasma membrane calcium channels and calcium release from intracellular stores is also blocked. Modification of calcium homeostasis is expected to have application in diseases of the nervous system involving modification of membrane lipids or transmitter release (Parkinson's, Alzheimer's), diseases of the cardiovascular system involving application of cardiac or vascular smooth muscle contractility and platelet aggregation (hypertension, cardiac infarction and atherosclerosis), diseases of the gastrointestinal tract such as ulcer disease, diarrhea, motility due to secretion of acid or $Cl^-$, diseases of the kidney involving renal handling of fluid and electrolytes (metabolic acidosis, alkalosis), and disease of abnormal growth (neoplasia, psoriasis).

The compounds of this invention have activity which is similar to that of manoalide, that is, the compounds appear to be devoid of the endocrine properties of the glucocorticoids while having anti-inflammatory and immunosuppressive properties.

In the methods of this invention, the compounds of Formulas I or IV are administered to mammals, including humans, in an effective amount to produce the desired activity, preferably in an amount of about 0.05 to 100 mg per day per kilogram of body weight. The amount of the compound depends upon the disease or condition being treated, the severity thereof, the route of administration and the nature of the host. The compounds may be administered topically, orally, parenterally or by other standard routes of administration.

Pharmaceutical compositions of this invention comprise compounds of Formula I or Formula IV and pharmaceutical carriers suitable for the route of administration. Standard methods for formulating pharmaceutical compositions of this type may be found in *Remington's Pharmaceutical Sciences,* Mack Publishing Company, Easton, Pa.

For topical administration, the pharmaceutical composition may be in the form of a salve, cream, ointment, spray, powder or the like. Standard pharmaceutical carriers for such compositions may be used. Preferably, compositions for topical administration will contain 0.05-5% of the active ingredient.

A typical cream formulation may contain the following:

| Ingredient | Parts by Weight |
| --- | --- |
| Water/glycol mixture (15% or more glycol) | 50-99 |
| Fatty alcohol | 1-20 |
| Non-ionic surfactant | 0-10 |
| Mineral oil | 0-10 |
| Typical pharmaceutical adjuvants | 0-5 |
| Active ingredient | 0.05-5 |

A typical ointment formulation may contain the following:

| Ingredients | Parts by Weight |
| --- | --- |
| White petrolatum | 40-94 |
| Mineral oil | 5-20 |
| Glycol solvent | 1-15 |
| Surfactant | 0-10 |
| Stabilizer | 0-10 |
| Active ingredient | 0.05-5 |

For oral administration, suitable pharmaceutical carriers include mannitol, lactose, starch, magnesium stearate, talcum, glucose and magnesium carbonate. Oral compositions may be in the form of tablets, capsules, powders, solutions, suspensions, sustained release formulations, and the like.

A typical tablet or capsule may contain the following:

| Ingredients | Percent w/w |
| --- | --- |
| Lactose, spray-dried | 40-99 |
| Magnesium stearate | 1-2 |
| Cornstarch | 10-20 |
| Active ingredient | 0.001-20 |

Parenteral compositions are prepared in conventional suspension or solution forms, as emulsions or as solid forms for reconstruction. Suitable carriers are water, saline, dextrose, Hank's solution, Ringer's solution, glycerol, and the like. Parenteral administration is usually by injection which may be subcutaneous, intramuscular or intravenous.

The compounds of this invention may be combined with other known anti-inflammatory/immunosuppressive agents such as steroids or non-steroidal anti-inflammatory agents (NSAID) in the pharmaceutical compositions and methods described herein.

The following examples are intended to illustrate the invention but are not limiting. All temperatures are in degrees Centigrade. NMR data are recorded in delta ppm.

2-Trimethylsilyl-4-furaldehyde n-Butyl lithium (a 2.5 m solution in hexane; 28.8 ml, 72 mmol) was added to a solution of morpholine (6.28 ml, 72 mmol) in tetrahydrofuran (700 ml) at −78° under argon. After 20 min., 3-furaldehyde (7.0 g, 72 mmol) was added. After another 20 min., sec-butyl lithium (a 1.3 m solution in cyclohexane; 55.4 ml, 72 mmol) was added dropwise and stirring continued at −780 for 7h before chlorotrimethylsilane (27 ml, 216 mmol) was added. Stirring continued overnight (14h) while the cooling bath was allowed to attain room temperature. The solution was poured into ice cold 10% (v/v) hydrochloric acid (200 ml) and after stirring at 0° for 10 min., the layers were separated. The aqueous phase was extracted with diethyl ether. All the organic phases were combined, dried (magnesium sulfate) and evaporated down to give a light brown oil, which was purified by flash chromatography on silica using 2% ethyl ether/hexane. Fractions with $R_f$ of about 0.30 (silica, 10% ethyl ether/hexane) on evaporation gave 8.22 g (68%) of the title aldehyde as a light yellow oil, bp 48°–50°/0.25 torr.

$^1$HNMR(CDCl$_3$) 0.29 (s,9H), 6.98 (s,1H), 8.25 (s,1H) and 9.95 (s,1H).

$^{13}$CNMR (CDCl$_3$)-2.0, 116.2, 128.9, 155.3, 164.1 and 184.5.

EXAMPLE 1

2-(3-Phenylpropyl)-2-butenal

To a stirred solution of lithium diisopropylamide (19.4 mmol) in 17 ml tetrahydrofuran (THF) at 0° under argon was added 2.3 ml 1,3-dimethyl-3,4,5,6-tetrahydro-2(1H)-pyrimidinone (DMPU), followed by the dropwise addition of crotonaldehyde cyclohexylimine (2.93 g, 19.4 mmol) in 3 ml THF. After 10 min. at room temperature the solution was cooled to −780 and stirred an additional 30 min., upon which time was added phenyl propyl bromide (3.2 ml, 21.3 mmol). After 4 hours at −78° the reaction mixture was quenched with saturated ammonium chloride solution, warmed to room temperature and extracted two times with ethyl ether. The organic portions were combined, washed twice with water, once with saturated ammonium chloride solution, dried over magnesium sulfate, filtered and concentrated to give the imine as a brown liquid. The imine was taken up in 10 ml ethyl ether and stirred with buffered acetic acid (10 ml, pH 4.5) for one hour, after which the solution was washed one time with water, two times with saturated sodium bicarbonate solution, one time with water, one time with saturated sodium chloride solution, dried over magnesium sulfate, filtered and concentrated. The residue was purified by flash chromatography (20% ethyl acetate/hexanes) to give the aldehyde as an orange oil.

IR (film): 1682, 1642 cm$^{-1}$.

$^1$H NMR, (CDCl$_3$): 9.36 (s, 1H); 7.20 (m, 5H); 6.54 (q, J=7.2 Hz, 1H); 2.61 (t, J=7.9 Hz, 2H); 2.30 (t, J=8.0 Hz, 2H); 1.91 (d, J=7.2 Hz, 3H); 1.67 (m, 2H).

$^{31}$C NMR (CDCl$_3$): 194.8, 150.0, 144.4, 141.9, 128.2 (strong), 125.7, 35.7, 29.9, 23.3, 14.7.

m/z Calculated for C$_{13}$H$_{16}$O: 188.1201, obtained (EI+): 188.1204.

2-(3-Phenylpropyl)-1-trimethylsilyloxy-,1,3-butadiene

A benzene (8 ml) solution of 2-(3-phenylpropyl)-2-butenal (2.53 g., 13.4 mmol), triethylamine (4.7 ml, 33.6 mmol) and fused zinc chloride (catalytic amount) was stirred at room temperature under argon for thirty minutes. Trimethylsilylchloride (3.4 ml, 26.8 mmol) was added and the mixture was stirred twenty hours at 50°, cooled and partitioned between cold hexane and cold saturated sodium bicarbonate solution. The aqueous portion was extracted again with cold hexane, and the combined organic portions were washed two times with cold saturated sodium bicarbonate, once with cold saturated sodium chloride, dried over magnesium sulfate, filtered and concentrated to give the enol ether as a brown oil. This material was used without further purification.

$^1$H NMR (CDCl$_3$): 7.23 (m, 5H); 6.42 (s. 1H); 6.19 (dd, J=10.8 and 6.7 Hz, 1H); 4.97 (d, J=16.6 Hz, 1H); 4.82 (d, J=10.8 Hz, 1H); 2.66 (t, 2H); 2.33 (t, 2H); 1.7 (m, 2H), 0.03 (s, 9H).

$^{13}$C NMR (CDCl$_3$): 142.9, 141.4, 135.8, 128.4, 128.2, 125.5, 122.9, 108.1, 35.9, 29.7, 23.1, −0.43.

5-(3-Fur-yl)-5-hydroxy-2-(3-phenylpropyl)-2-pentenal

To a stirred solution of 2-(3-phenylpropyl)-1-trimethylsilyloxy-1,3-butadiene (1.44 g., 5.54 mmol) and furaldehyde (0.54 g, 5.6 mmol) in 40 ml methylene chloride at −55° under argon was added boron trifluoride etherate (0.69 ml, 5.6 mmol). After 18 hours the reaction mixture was quenched with saturated sodium bicarbonate solution and warmed to room temperature. The resulting mixture was partitioned between methylene chloride and saturated sodium bicarbonate solution. The organic portion was washed once with sodium bicarbonate, once with water, once with saturated sodium chloride solution, dried over magnesium sulfate, filtered and concentrated to give a dark oil. This was purified by flash chromatography (7:3 to 3:2 hexane/ethyl acetate) to give the desired hydroxy aldehyde.

IR (film): 3425 (broad), 1670, 1635 cm$^{-1}$.

$^1$H NMR (CDCl$_3$): 9.36 (s, 1H); 7.14–7.40 (m, 6H); 6.53 (t, J=7.2 Hz, 1H); 7.37 (s, 1H); 4.82 (t, J=6.3 Hz, 1H); 2.72 (m, 2H); 2.60 (t, J=7.9 Hz, 2H); 2.23 (m, 2H); 1.65 (m, 2H).

$^{13}$C NMR CDCl$_3$: 194.9, 150.0, 149.9, 145.1, 143.9, 141.8, 139.1, 128.6, 128.3, 125.8, 108.2, 65.7, 37.0, 35.7, 30.0, 23.8.

m/z calculated for C$_{18}$H$_{20}$O$_3$: 284.1828. Obtained (EI+): 284.1831.

3,6-Dihydro-2-(3-furyl)-6-hydroxy-5-(3-phenylpropyl)-2H-pyran 5-(3-Furyl)-5-hydroxy-2-(3-phenylpropyl)-2-pentenal (0.254 g., 0.894 mmol) was dissolved in 80 ml benzene, placed i-n a quartz tube and subjected to two freeze, pump, thaw cycles. The tube was flushed with argon and irradiated at 254 nm for ten hours. The solution was then cooled and concentrated to give a mixture of the acetal and starting aldehyde as an orange gum. The mixture was separated by flash chromatography (7:3 hexane/ethyl acetate) to give the desired hydroxy acetal as a yellow oil (which solidified on standing) and the starting hydroxy aldehyde.

IR(film): 3400 (br) cm$^{-1}$.

$^1$H NMR (CDCl$_3$): 7.45 (s, 1H); 7.42 (s, 1H); 7.26 (m, 5H), 6.45 (s, 1H); 5.75 (m, 1H); 5.34 and 5.31 (2s, 1H); 5.00 (m, 1H); 3.0 (bs, 1H); 2.67 (t, 2H); 2.1 to 2.4 (m. 4H); 1.8 (m, 2H).

$^{13}$C NMR (CDCl$_3$): 143.2, 142.1, 139.1, 136.1, 128.3, 128.2, 125.7, 122.4, 122.3, 108.8, 93.6, 62.4, 35.5, 31.9, 31.3, 28.9.

m/z calculated for C$_{18}$H$_{20}$O$_3$: 284.1413, obtained (EI+): 284.1415.

4-[3,6-Dihydro-6-hydroxy-5-(3-phenylpropyl)-2H-pyran-2-yl]-5-hydroxy-2(5H)-furanone and

3-[3,6-Dihydro-6-hydroxy-5-(3-phenylpropyl)-2H-pyran-2-yl]-5-hydroxy-2(5H)-furanone A stirred solution of 3,6-dihydro-2-(3-furyl)-6-hydroxy-5-(3-phenylpropyl)-2H-pyran (0.102 g., 0.359 mmol) and Rose Bengal (trace) in 100 ml methanol was flushed with oxygen for 10 minutes and cooled to −78°. The pink solution was irradiated for two hours with a 150 W high intensity lamp, warmed to room temperature and concentrated to an oil. This material was purified by flash chromatography (7:3 methylene chloride/ethyl acetate) to give a regioisomeric mixture of two hydroxybutenolides as a pinkish gum. The mixture was separated by semi-preparative HPLC on a Whatman Partisil M-9 silica column, with an elution rate of 4 ml/min with 60% methylene chloride/ethyl acetate. The above titled 4-(substituted pyranyl)-5-hydroxy-2(5H)-furanone was eluted at 11.5 minutes, followed by the above titled 3-(substituted cyranyl)-5-hydroxy-2(5H)-furanone at 12.5 minutes. Concentration gave the purified compounds as a clear glass.

4-pyranyl isomer

IR(CHCl$_3$): 3440 (br), 1790 (sh), 1764 cm$^{-1}$.

$^1$H NMR (as mixture of diasteriomers) (CDCl$_3$): 7.27 (m, 5H); 6.1 (m, 2H); 5.70 (brs, 1H); 5.31 (2s, 1H); 4.88 (m, 1H); 2.64 (t, J=7.6 Hz, 2H); 2.2 (m, 4H); 1.75 (m).

$^{13}$C NMR (as mixture of diasteriomers) (CDCl$_3$): 170.3, 167.8, 142.0, 137.3. 128.3, 125.8, 121.0 and 120.8, 118.4, 117.4, 97.6 and 97.2, 91.5 and 91.3, 63.1 and 62.4, 35.5, 32.0, 29.1 and 29.0, 28.7.

m/z Calculated for C$_{18}$H$_{18}$O$_4$ (M+-H$_2$O): 298.1205, obtained (EI+): 298.1188.

3-pyranyl isomer

IR(CHCl$_3$): 3400, 1765 cm$^{-1}$.

$^1$H NMR (as mixture of diasteriomers) (CDCl3): 7.22 (m, 5H); 7.12 (s, 1H); 6.12 (m, 1H); 5.68 (brs, 1H); 5.26 (m, 1H); 4.8 (m, ]H); 4.1 (brs, 1H) 2.63 (t, 2H); 2.4 (m, 1H); 2.12 (m, 3H); 1.8 (m, 2H).

m/z Calculated for C$_{18}$H$_{18}$O$_4$ (M+-H$_2$O): 298.1205, obtained (EI+): 298.1206.

EXAMPLE 2

3,6-Dihydro-2-(3-furyl)-6-methoxy-5-(3-phenylpropyl)-2H-pyran

A solution of 5-(3-furyl)-5-hydroxy-2-(3-phenylpropyl)-2-pentenal (0.286 g., 1.01 mmol), prepared as in Example 1, and p-toluene sulfonic acid (catalytic amount) in 12 ml methanol was heated to reflux temperature for 1.5 hours. The solution was concentrated, diluted with methylene chloride and passed through a neutral alumina column (8:2 hexane/ethyl ether). The methoxy acetal was obtained as a yellow oil.

IR(film): 1605, 1500 cm$^{-1}$.

$^1$H NMR (CDCl$_3$): 7.43 (s, 1H); 7.39 (d, J.1.4 Hz, 1H); 7.23 (m, 5H); 6.43 (d, J=1.4 Hz, 1H); 5.70 (brd, 1H); 4.85 (dd, J=4.0, 10.8 Hz, 1H); 4.80 (s, 1H); 3.45 (s. 3H); 2.64 (t, J=7.6 Hz, 2H); 2.2 (m, 2H); 1.8 (m, 2H).

$^{13}$C NMR (CDCl$_3$): 143.6, 142.6, 139.7, 136.6, 128.7, 128.6, 126.8, 126.1, 122.4, 109.3, 98.9, 61.8, 55.8, 35.9, 32.5, 31.4, 29.5.

m/z Calculated for C$_{19}$H$_{22}$O$_3$: 298.1569, obtained (EI): 298.1547.

4-[3,6-Dihydro-6-methoxy-5-(3-phenylpropyl)-2H-pyran-2yl]-5-hydroxy-2(5H)-furanone and 3-[3,5-Dihydro-6-methoxy-5-(3-phenylpropyl)-2H-pyran-2yl]-5-hydroxy-2(5H)-furanone.

A stirred solution of 3,6-dihydro-2-(3-furyl)-6-methoxy-5-(3-phenylpropyl)-2H-pyran (0.263 g., 0.88 mmol) and Rose Bengal (trace) in 200 ml methanol was flushed with oxygen and cooled to −780. The pink solution was irradiated for 2.5 hours with a 200 W tungsten lightbulb, warmed to room temperature and concentrated to an oil. This material was purified by flash chromatography (1:1 ethyl acetate/hexane) to give a regioisomeric mixture of two hydroxy butenolides as an orangish gum. The mixture was separated by semi-preparative HPLC on a Whatman Partisil M-9 silica column, with an elution rate of 4 ml/min with 30% ethyl acetate/methylene chloride. The above titled 4-(substituted pyranyl)-5-hydroxy-2(5H)-furanone was eluted at 17 minutes, followed by the above titled 3-(substituted pyranyl)-5-hydroxy-2(5H)-furanone at 19 minutes. Concentration gave the purified compounds as clear glasses, which solidified on standing.

4-pyranyl isomer

IR(CHCl$_3$): 3580, 3350 (br), 1790 (sh), 1765, 1655, 1605, cm$^{-1}$.

$^1$H NMR (as mixture of diasteriomers) (CDCl$_3$): 7.2 (m, 5H); 6.03–6.26 (m, 2H); 5.68 (brs, 1H); 4.78 (m, 2H); 4.65 (brs, 1H); 3.45 and 3.43 (two s, 3H); 2.63 (t, 2H); 2.1–2.3 (m, 4H); 1.78 (p, 2H).

$^{13}$C NMR (as mixture of diasteriomers) (CDCl$_3$): 167.5, 167.3, 142.1, 136.7 and 136.5, 128.4, 125.8, 120.9 and 120.7, 118.3 and 117.4, 107.4, 98.4 and 98.3, 97.7 and 97.1, 63.1 and 62.2, 55.8 and 55.7, 35.5, 32.1, 29.0.

m/z calculated for C$_{19}$H$_{22}$O$_5$: 330.1467, obtained (EI+): 330.1452.

3-pyranyl isomer

IR(CHCl$_3$): 3570, 3350 (br), 1762, 1595 cm$^{-1}$.

$^1$H NMR (as mixture of diasteriomers) (CDCl$_3$): 1 7.2 (m, 5H); 7.14 (s, 1H); 6.15 (s, 1H); 5.67 (d, J=5.4 Hz, 1H); 4.77 (s, 1H); 4.69 (brd, 1H); 4.18 (brs, 1H); 3.43 and 3.42 (two s, 3H); 2.63 (t, J=6.6 Hz, 2H); 2.45 (m, 1H); 2.07 (m, 3H); 1.78 (p, 2H).

$^{13}$C NMR (as mixture of diasteriomers) (CDCl$_3$): 169.3, 143.8, 142.2, 138.9. 136.2, 128.4. 128.3, 125.7, 121.4, 98.4, 97.0 and 96.9, 61.9 and 61.7, 55.7 and 55.6, 35.5, 32.1. 29.6, 29.1.

m/z Calculated for C$_{19}$H$_{22}$O$_5$: 330.1467, obtained (EI+): 330.1471.

EXAMPLE 3

2-Methyl-1-trimethylsilyloxy-1,3-butadiene

To a stirred solution of tiglic aldehyde (3 ml, 31 mmol), triethylamine (10 ml, 72 mmol) and ZnCl (catalytic amount, fused) in 15 ml benzene at room temperature under argon was added trimethylsilylchloride (7.8 ml, 62 mmol). The resulting brown suspension was stirred at 50° for 15 hours, cooled to room temperature and partitioned between cold pentane and saturated sodium bicarbonate solution. The organic portion was washed two times with sodium bicarbonate solution and the aqueous portions were combined and extracted again with pentane. The pentane portions were then combined, washed again once with saturated sodium bicarbonate solution, once with saturated sodium chloride solution, dried over magnesium sulfate, filtered and concentrated carefully until about 25 ml of solution remained. This residue was distilled at atmospheric pressure to give the desired enol ether (bp 150°).

$^1$H NMR (CDCl$_3$): 6.40 (d, J=2 Hz, 1H); 6.30 (dd, J=17 and 11 Hz, 1H); 5.00 (dd, J=17 and 2 Hz, 1H); 4.84 (dd, J=11 and 2 Hz, 1H); 1.72 (d, J.2H, 3H); 0.22 (s, 9H).

$^{13}$C NMR (CDCl$_3$): 141.2, 137.0, 118.9, 108.3, 8.7, −0.5.

5-Hydroxy-2-methyl-5-(2-trimethylsilylfuran-4-yl)-2-pentenal

To a stirred solution of 5-trimethylsilyl-3-furaldehyde (0.382 g., 2.27 mmol) in dry methylene chloride (15 ml) at −50° under argon was added dropwise boron trifloride etherate (0.28 ml, 2.3 mmol). This addition was followed by the dropwise addition of 2-methyl-l-trimethylsilyloxy-1,3-butadiene (0.356 g., 2.3 mmol). The solution was stirred at −50° to −60° for 18 hours, quenched by the addition of several ml saturated sodium bicarbonate solution, warmed to room temperature and poured into methylene chloride. The organic portion was washed once with saturated bicarbonate solution, once with water, once with saturated sodium chloride solution, dried over magnesium sulfate, filtered and concentrated to give a yellow oil which consisted of several components by TLC. The mixture was applied to a chromatography column (silica) and eluted with 30% ethyl acetate/hexane. Eluted last was the desired alcohol, which was concentrated to give a yellow gum.

IR(CHCl$_3$): 3600, 1685, 1645 cm$^{-1}$.

$^1$H NMR (CDCl$_3$): 9.34 (s, 1H); 7.53 (s, 1H); 6.57 (s, 1H); 6.52 (t, J=6 Hz, 1H); 4.81 (t, J=6 Hz, 1H); 2.73 (m, 2H); 1.95 (brs, 1H); 1.68 (s, 3H); 0.19 (s, 9H).

$^{13}$C NMR (CDCl$_3$): 195.2, 162.2, 149.7, 143.3. 141.1, 128.2, 117.9, 65.8, 37.4, 9.5, −1.7.

m/z Calculated for C$_{13}$H$_{20}$O$_3$Si: 252.1182, obtained (EI+): 252.1184.

3,6-Dihydro-6-hydroxy-5-methyl-2-[3-(2-trimethylsilylfuryl)]-2H-pyran

5-Hydroxy-2-methyl-5-[3-(2-trimethylsilylfuryl)]-2-pentenal (0.099 g., 0.394 mmol) was dissolved in 40 ml dry benzene, placed in a quartz tube, flushed with oxygen free nitrogen for 0.5 hours and irradiated at 254 nm for four hours. The solution was cooled and concentrated to give a yellow oil. Purification by flash chromatography (20–30% ethyl acetate/hexane) yielded the acetal along with starting aldehyde. $^1$H NMR (CDCl$_3$): 7.65 (s, 1H); 6.68 (s. 1H); 5.72 (brs, 1H); 5.25 (brs, 1H); 4.98 (m, 1H); 3.44 (brs, 1H); 2.4–2.1 (m, 2H); 1.74 (s, 3H); 0.25 (s, 9H).

4-(3.6-Dihydro-6-hydroxy-5-methyl-2H-Pyran-2-yl)-5-hydroxy-2(5H)-furanone

A stirred solution of 3,6-dihydro-6-hydroxy-5-methyl-2-[3-(2-trimethylsilylfuryl)]-2H-pyran (0.104 g., 0.414 mmol) and Rose Bengal (trace) in 50 ml methanol was flushed with oxygen for 5 minutes and cooled to −78°. The pink solution was irradiated for 1.5 hours with a 150 W lamp, warmed to room temperature and concentrated to an oil. This material was purified by flash chromatography (1:1 methylene chloride/ethyl acetate) to give the hydroxybutenolide as a clear oil which solidified on standing.

IR(CHCl$_3$): 3350 (br), 1780 (sh), 1760, 1655 cm$^{-1}$.

$^1$H NMR (CDCl$_3$): 6.38 (brs, 1H); 6.10 (m, 2H); 5.70 (brs, 1H); 5.25 (brd, 1H); 5.05 (brs, 1H); 4.88 (m, 1H); 2.25 (m, 2H); 1.78 (s, 3H).

Calculated for C$_{10}$H$_{16}$O$_5$N (M+ +NH$_4$+): 230.1028, obtained (CI+): 230.1038.

EXAMPLE 4

2-]6-(Benzo[b]thien-2-yl)-hexyl]-2-butenal

To a stirred solution of lithium diisopropylamide (4.9 mmol) in 4 ml tetrahydrofuran at 0° under argon was added 1,3-dimethyl-3,4,5,6-tetrahydro-2(1H)-pyrimidinone (DMPU) (0.6 ml, 5.1 mmol), followed by the dropwise addition of crotonaldehyde cyclohexylimine (0.746 g., 4.9 mmol) in 1 ml tetrahydrofuran. After 10 minutes at 0° the solution was cooled to −78° and stirred an additional 30 minutes, upon which time was added 6-(benzo[b]thien-2-yl)-1-bromohexane (1.6 g., 5.4 mmol) in 1.5 ml tetrahydrofuran. An additional 1 ml tetrahydrofuran was added after 45 minutes to solubilize the mixture. After 5 hours at −78°, the reaction mixture was quenched with saturated ammonium chloride solution, warmed to room temperature, and extracted two times with ethyl ether. The organic portions were combined, washed twice with water, once with saturated sodium chloride, dried over magnesium sulfate, filtered and concentrated to give the imine as an orange oil. The imine was taken up in 50 ml ethyl ether and stirred with buffered acetic acid (20 ml, pH 4.5) for 45 minutes, after which the solution was washed one time with water, two times with saturated sodium bicarbonate solution, one time with water, one time with saturated sodium chloride solution, dried over magnesium sulfate, filtered and concentrated. The residue was purified by flash chromatography (silica, 10 to 20% ethyl acetate/hexane). First eluted was the starting bromide followed by the title aldehyde.

IR(CHCl$_3$): 1675, 1645 cm$^{-1}$.

$^1$H NMR (CDCl$_3$): 9.36 (s, 1H); 7.76 (d, J=7.7 Hz, 1H); 7.66 (d, J=7.2 Hz, 1H); 7.26 (m, 2H); 6.99 (s, 1H); 6.54 (q, J=7.3 Hz, 1H); 2.89 (t, J=7.5 Hz, 2H); 2.25 (m, 2H); 1.96 (d, J=7.3 Hz, 3H); 1.74 (m, 2H); 1.36 (m, 6H).

$^{13}$C NMR (CDCl$_3$): 1 195.0, 149.6, 146.7, 144.9, 140.2, 139.3, 124.0, 123.3, 122.6, 122.1, 120.4, 31.0, 30.7. 29.3, 28.9, 28.3. 23.6, 14.7.

m/z Calculated for C$_{18}$H$_{22}$H OS: 286.1391, obtained (EI+): 286.1379.

2-[6-(Benzo[b]thien-2-yl)-hexyl]-1-trimethylsilyloxy-1,3-butadiene

A benzene (2 ml) solution of 2-[6-(benzo[b]thien-2-yl)-hexyl]-2-butenal (0.558 g., 1.95 mmol), triethylamine (0.68 ml, 4.9 mmol) and fused zinc chloride (catalytic amount) was stirred at room temperature under argon. Trimethylsilylchloride (0.5 ml, 4 mmol) was added and the mixture was stirred twenty hours at room temperature, then partitioned between cold hexane and cold saturated sodium bicarbonate solution. The aqueous portion was extracted again with cold hexane, and the combined organic portions were washed two times with cold, saturated sodium bicarbonate, once with cold, saturated sodium chloride, dried over magnesium sulfate, filtered and concentrated to give the enol ether as a yellow liquid. This material was used without further purification.

$^1$H NMR (CDCl$_3$): 7.76 (d, J=7.7 Hz, 1H); 7.66 (d, J=7.7 Hz, 1H); 7.3 (m, 2H); 6.99 (s, 1H); 6.38 (s, 1H); 6.17 (m, 1H); 5.01 (dd, J=17.8 and 2 Hz, 1H); 4.83 (dd, J=10.8 and 2 Hz, 1H); 2.90 (t, J=7 Hz, 2H); 2.25 (m, 2H); 1.75 (m, 2H); 1.4 (m, 6H); 0.21 (s, 9H).

$^{13}$C NMR (CDCl$_3$): 146.9, 141.1, 140.2, 139.3, 135.9, 124.0, 123.3, 122.6, 122.1, 120.3, 108.2, 31.2, 30.8, 29.3, 29.0. 27.9, 23.2, −0.47.

2-[6-(Benzo[b]thien-2-yl)-hexyl]-5-hydroxy-5-(2-trimethylsilyl-4-furyl)-2-pentenal To a stirred solution of 5-trimethylsilyl-3-furaldehyde (0.282 g., 1.7 mmol) in 5 ml methylene chloride at −60° under argon was added dropwise boron trifluoride etherate (0.2 ml, 1.62 mmol). After 5 minutes a solution of 2-[6-(benzo[b]thien-2-yl)-hexyl]-1-trimethylsilyl oxy-1,3-butadiene (0.584 g., 1.63 mmol) in 2 ml methylene chloride was added dropwise. The solution was stirred for 20 hours at °60°, quenched with saturated sodium bicarbonate solution, warmed to room temperature, and taken up in ethyl ether. The organic portion was washed twice with saturated sodium bicarbonate, once with water, once with saturated sodium chloride solution, dried over magnesium sulfate, and concentrated to give an orange oil which was a complex mixture by TLC. The mixture was purified by flash chromatography (silica, 25% ethyl acetate/hexane). First eluted was 2-[6-(benzo[b]thien-2-yl)-hexyl]-2- butenal followed by the title hydroxy aldehyde as a yellow oil.

IR(CHCl$_3$): 3600, 1680, 1645 cm$^{-1}$.

$^1$H NMR (CDCl$_3$): 9.32 (s, 1H); 7.71 (d, J=7.7 Hz, 1H); 7.62 (d, J=7.5 Hz, 1H); 7.56 (s, 1H); 7.25 (m, 2H); 6.96 (s, 1H); 6.62 (s, 1H); 6.5 (m, 1H); 4.8 (m, 1H); 2.85 (m, 4H); 2.21 (m, H); 1.7 (m, 3H); 1.35 (m); 0.25 (s, 9H).

$^{13}$C NMR (CDCl$_3$): 194.9, 161.8, 150.0, 146.5, 145.2, 143.1, 140.1, 139.2, 128.2, 123.9, 123.2, 122.5, 121.9, 120.3, 117.9, 65.7, 37.2, 30.9, 30.6, 29.3, 28.7, 28.3, 24.1, −1.8.

m/z Calculated for C$_{26}$H$_{34}$O$_3$SSi: 454.2000, obtained (EI+): 454.1994.

5-[6-(Benzo[b]thien-2-yl)-hexyl]-3,6-dihydro-6-hydroxy-2-(2-trimethylsilyl-4-furyl)-2H-pyran 2-(6-(Benzo(b]thien-2-yl)-hexyl]-5-hydroxy-5-(2-trimethylsilyl-4-furyl)-2-pentenal (0.142 g., 0.31 mmol) was dissolved in 30 ml anhydrous benzene, placed in a quartz tube, and subjected to four freeze, pump, thaw cycles. The tube was flushed with argon and irradiated at 254 nm for 2.5 hours. The solution was concentrated to give an orange gum. This material was purified by flash chromatography (silica, 5 to 30% ethyl acetate/hexane. First eluted was the desired hydroxy acetal as a yellow gum. Second eluted was starting aldehyde as a clear gum.

IR(CHCl$_3$): 3600 (weak), 2940, 1675 cm$^{-1}$.

$^1$H NMR (CDCl$_3$): 7.6 to 7.7 (m, 3H); 7.2 to 7.3 (m, 2H); 7.01 (s, 1H); 6.69 (s, 1H); 5.71 (m, 1H); 5.33 (brs, 1H); 4.98 (m, 1H); 2.92 (m, 2H); 2.0 to 2.4 (m, 4H); 1.6 to 1.8 (m, 2H); 1.4 (m, 6H); 0.23 (s, 9H).

$^{13}$C NMR (CDCl$_3$): 161.4, 155.9, 146.7, 143.6, 140.2, 139.2, 137.0, 126.2, 124.0, 123.3, 122.6, 122.1, 120.4, 118.6, 91.8, 61.6, 32.5, 31.4, 31.0, 30.7, 29.1, 28.9, 28.8, 27.3, −1.7.

M+ observed for C$_{26}$H$_{34}$O$_3$SSi: 454.

4-[5-(6-(Benzo[b]thien-2-yl)-hexyl)-3,6-dihydro-6-hydroxy-2H-pyran-2-yl]-5-hydroxy-2(5H)-furanone A stirred solution of 5-[6-benzo(b]thien-2-yl)-hexyl]-3,6-dihydro-6-hydroxy-2-(2-trimethylsilyl-4-furyl)-2H-pyran (23 mg., 0.05 mmol) and Rose Bengal (trace) in 10 ml methylene chloride (solubilized with 9 drops methanol) was flushed with oxygen and cooled to −78°. The pink solution was irradiated for 30 minutes with a 150 W flood lamp, warmed to room temperature and concentrated to a yellow gum. This material was purified by flash chromatography (silica, 1:1 hexanex/ethyl acetate) to give the hydroxybutenolide as a clear oil.

IR(CHCl$_3$): 3600, 3350 (broad), 1770 cm$^{-1}$.

$^1$H NMR (CDCl$_1$ ): 7.77 (d, J=7.6 Hz, 1H); 7.67 (d, J=7.2 Hz, 1H); 7.3 (m, 2H); 7.00 (s, ]H); 6.1 (m, 2H); 5.69 (brs, 1H); 5.34 (s, 1H); 4.8 (m, 1H); 2.89 (t, 2H); 1.9 to 2.3 (m, 4H); 1.7 (m), 1.3 (m).

m/z Calculated for C$_{23}$H$_{24}$O$_4$S (M+-H$_2$O): 396.1395, obtained (EI+): 396.1410.

EXAMPLE 5

2-(4-methyl-3-pentenyl)-2-butenal

To a stirred solution of lithium diisopropyl amide (14.0 mmol) in 10 ml tetrahydrofuran (THF) at −10° under argon was added 1,3-dimethyl-3,4,5,6-tetrahydro-2(1H)-pyrimidinone (DMPU) (1.7 ml, 14.0 mmol), followed after 45 minutes by the dropwise addition of crotonaldehyde cyclohexylimine (1.9 g, 12.7 mmol) in 2 ml THF. After 10 minutes at 0° the solution was cooled to −78° and stirred an additional 30 minutes, upon which time was added 1-bromo-4-methyl-3-pentene (2.49 g., 15.3 mmol) in 1 ml THF. After 4.5 hours at −70° to −65°, the reaction mixture was quenched with saturated ammonium chloride solution, warmed to room temperature, and extracted two times with ethyl ether. The organic portions were combined, washed four times with water, once with saturated sodium chloride, dried over magnesium sulfate and filtered. This ethyl ether solution was subsequently stirred for two hours at room temperature with 25 ml buffered acetic acid solution (pH 4.5). The organic portion was then washed twice with water, once with saturated sodium bicarbonate solution, once with sodium chloride solution, dried over magnesium sulfate, filtered and distilled at atmospheric pressure until about 25 ml of solution remained in the still pot. The residue was purified by flash chromatography (silica, 5 to 10% ethyl ether/hexane), the desired fractions were concentrated by distillation, and the residue was distilled (Kujelrohr, 25 mm 85° to 90°) to give the purified aldehyde as a pale yellow, volatile liquid.

IR (CHCl$_3$): 1680, 1642 cm$^1$.

$^1$H NMR (CDCl$_3$): 9.39 (s, 1H); 6.60 (q, J=7.3 Hz, 1H): 5.13 (bt, 1H); 2.30 (m, 2H); 2.06 (m, 2H); 2.01 (d, J=7.3 Hz, 3H); 1.69 (s, 3H); 1.60 (s, 3H).

$^{13}$C NMR (CDCl$_3$): 194.9, 149. 8, 144.4, 132.3, 123.5, 26.8. 25.6, 23.7, 17.5, 14.8.

2-(4-Methyl-3-pentenyl)-1-trimethylsilyloxy-1,3-butadiene

A benzene (4 ml) solution of 2-(4-methyl-3-pentenyl)-2-butenal (0.79 g., 5.2 mmol), triethylamine (1.8 ml, 13 mmol) and fused zinc chloride (catalytic amount) was stirred at room temperature under argon. Trimethylsilylchloride (1.3 ml, 10 mmol) was added and the mixture was stirred for twenty hours, then partitioned between cold pentane and cold saturated sodium bicarbonate solution. The aqueous layer was extracted again with cold pentane, and the combined organic portions were washed two times with cold, saturated sodium bicarbonate, once with cold saturated sodium chloride, dried over magnesium sulfate, filtered and concentrated by distillation of volatile solvents. The residue was carefully concentrated further on the rotary evaporator to give the enol ether as a yellow oil.

$^1$H NMR (CDCl$_3$): 6.39 (s, 1H); 6.20 (dd, J=10.8 and 17.2 Hz, 1H); 5.21 (bt, 1H); 5.05 (d, J.16 Hz, 1H); 4.84 (d, J=10 Hz, 1H); 2.26 (m, 2H); 2.09 (m, 2H); 1.71 (s, 3H); 1.63 (s, 3H); 0.22 (s, 9H).

$^{13}$C NMR (CDCl$_3$): 141.2, 135.7, 131.3, 124.8, 123.0, 107.9, 26.8, 25.7, 23.8, 23.6, 17.5, −0.5.

5-Hydroxy-2-(4-methyl-3-pentenyl)-5-(2-trimethylsilyl-4-furyl)-2-pentenal

To a stirred solution of 5-trimethylsilyl-3-furanaldehyde (0.444 g, 2.6 mmol) in 5 ml methylene chloride at −60° under argon was added dropwise boron trifluoride etherate (0.33 ml, 2.7 mmol). After one to two minutes a solution of 2-(4-methyl-3-pentenyl)-1-trimethylsilyloxy-1,3-butadiene (0.604 g, 2.7 mmol) in 3 ml methylene chloride was added dropwise. The solution was stirred for 20 hours at −60°, quenched with saturated sodium bicarbonate solution, warmed to room temperature, and taken up in ethyl ether. The organic portion was washed twice with saturated sodium chloride solution, dried over magnesium sulfate, filtered and concentrated to give an orange oil which was complex by TLC. The mixture was purified by flash chromatography (silica, 30% ethyl acetate/hexane). Eluted last was the desired hydroxyaldehyde as an orange oil.

IR (film): 3420 (broad), 1685, 1645 cm$^{-1}$.

$^1$H NMR (CDCl$_3$): 9.38 (s, 1H); 7.61 (s, 1H); 6.66 (s, 1H); 6.58 (t, J=7 Hz, 1H); 5.11 (bt, 1H); 4.87 (t, J=6 Hz, 1H); 2.84 (m, 2H); 2.29 (m, 3H); 2.05 (m, 1H); 1.69 (s, 3H); 1.58 (s, 3H); 0.28 (s, 9H).

$^{13}$C NMR (CDCl$_3$): 195.0, 162.0, 150.3, 144.7, 143.1, 132.4, 128.1. 123.3, 117.8, 65.7, 37.3, 26.8, 25.6, 24.3, 17.6, −1.8.

m/z Calculated for C$_{18}$H$_{28}$O$_3$Si: 320.1808. Obtained (EI+): 320.1805.

3,6-Dihydro-6-hydroxy-5-(4-methyl-3-pentenyl)-2-(2-trimethylsilyl-4-furyl)-2H-pyran 5-Hydroxy-2-(4-methyl-3-pentenyl)-5-(2-trimethylsilyl-4-furyl)-2-pentenal (0.88 g, 0.274 mmol) was dissolved in 27 ml anhydrous benzene, placed in a quartz tube and deoxygenated by saturating with oxygen-free nitrogen for one hour. The solution was irradiated at 254 nm for three hours, cooled and concentrated to give a brown-yellow gum. This material was purified by flash chromatography (silica, 15 to 30% ethyl acetate/hexane). First eluted was the desired acetal followed by starting aldehyde.

IR (CHCl$_3$): 3600, 1250 cm$^{-1}$.

$^1$H NMR (CDCl$_3$): 7.64 (d, J=1.7 Hz, 1H); 6.69 (d, J=1.6 Hz, 1H); 5.75 (bd, 1H); 5.34 (bs, 1H); 5.14 (bs, 1H); 4.99 (m, 1H); 2.98 (bs, 1H); 2.38 (bt, 1H); 2.16 (m, 5H); 1.71 (s, 3H); 1.64 (s, 3H); 0.26 (s. 9H).

$^{13}$C NMR (CDCl$_3$): 143.7, 136.8, 132.0, 126.2, 126.1, 123.8, 122.3, 118.6, 91.8, 61.6, 32.6, 31.4, 26.2. 25.7, 17.7, −1.7.

m/z calculated for C$_{18}$H$_{28}$O$_3$Si: 320.1808. Obtained (EI+): 320.1815.

5-Hydroxy-4-[3,6-dihydro-6-hydroxy-5-(4-methyl-3-pentenyl)-2H-pyran]-2(5H)-furanone A stirred solution of 3,6-dihydro-5-(4-methyl-3-pentenyl)-2-(2-trimethylsilyl-4-furyl)-2H-pyran (0.026 g, 0.081 mmol) and Rose Bengal (trace) in 15 ml methylene chloride (solubilized with 5 drops methanol) was flushed with oxygen and cooled to −78°. The pink solution was irradiated for 35 minutes with a 150 watt flood lamp, warmed to room temperature and concentrated to an orange gum. This material was purified by flash chromatography (silica, 50% ethyl acetate/hexanes) to give the hydroxybutenolide as a clear gum.

IR (CHCl$_3$) 3400 (broad), 1760 cm$^{-1}$.

$^1$H NMR (CDCl$_3$): 6.03 to 6.27 (m, 2H); 5.8 (brs, 1H); 5.72 (brs, 1H); 5.33 (d, 1H); 5.11 (brs, 1H); 4.9 (m, 1H); 4.35 (brs, 1H); 2.14 (m, 6H); 1.70 (s, 3H); 1.62 (s, 3H).

$^{13}$C NMR (mixture of diastereomers) (CDCl$_3$): 171.2 and 170.9, 168.3 and 167.7, 137.4 and 137.2, 132.3, 123.6, 121.1 and 120.8, 118.3 and 117.3, 97.9 and 97.6, 91.7 and 91.5, 63.2 and 62.4, 32.6, 29.2 and 28.7, 26.1, 25.7, 17.8.

m/z calculated for C$_{15}$H$_{19}$O$_5$ (M-H)$^+$: 279.1221. Obtained (EI+): 279.1222.

EXAMPLE 6

Methyl 2-cyclohexyl-3-hydroxypropionate

To a stirred solution of diisopropylamine (0.85 ml, 6.10 mmol) in 30 ml tetrahydrofuran at −78° under argon was added n-butyllithium (2.5 ml of a 2.5M solution in hexane). After 0.5 hour, methyl cyclohexylacetate (1 ml, 6.10 mmol) was added dropwise in 10 ml tetrahydrofuran. The solution was stirred for 45 minutes, after which was added acetaldehyde (1 ml) in 10 ml tetrahydrofuran. This solution was stirred for two hours at −78°, warmed to room temperature and stirred an additional 12 hours, quenched with water and acidified with 10% hydrochloric acid. The mixture was extracted twice with ethyl ether, and the combined organic portions were then washed once with 10% hydrochloric acid, twice with water, once with saturated sodium chloride solution, dried over magnesium sulfate, filtered and concentrated to give the alcohol as an orange oil (b.p. 85°−92°, 0.5 mm).

IR(film): 3450 (br), 1738, 1715 (sh) cm$^1$.

$^1$H NMR (CDCl$_3$): Partial, 4.14 (p, J=6.5 Hz, 1H); 3.70 (s, 3H); 2.39 (t, J=6.5 Hz, 1H); 2.25 (brs, 1H); 1.24 (d, J=6.5 Hz, 3H).

$^{13}$C NMR (CDCl$_3$): 174.3, 66.3, 58.2, 51.1, 36.6, 31.7, 30.2, 26.4. 26.3, 26.2. 20.3.

Calculated for C$_{11}$H$_{21}$O$_3$ (MH+): 201.1490, obtained (EI+) 201.1494.

Methyl 2-cyclohexyl-2-propenoate

To a stirred solution of methyl 2-cyclohexyl-3-hydroxypropionate (0.836 g., 4.16 mmol) in 5 ml pyridine at 0° under argon was added methanesulfonyl chloride (0.48 ml, 6.24 mmol). The mixture was stirred for one hour at 00, then warmed to room temperature and stirred an additional 20 hours, during which time a brownish color formed. The reaction mixture was poured into ethyl ether and water, and the aqueous portion was extracted again with ethyl ether. The combined organic portions were washed twice with water, three times with 10% copper sulfate, three times with water, once with saturated sodium bicarbonate solution, once with sodium chloride solution, dried over magnesium sulfate, filtered and concentrated to give the mesylate as a yellow oil. This material was used without further purification.

A 1 ml solution of the mesylate (0.437 g., 1.57 mmol) in methanol was added to a solution of sodium methoxide (prepared from 37 mg sodium and 25 ml methanol) at room temperature under argon. After three hours the temperature was raised to 60° and the mixture was stirred for an additional 1.5 hours. The solution was cooled, and most of the methanol distilled away at atmospheric pressure. The residue was partitioned between ethyl ether and water, and the aqueous portion was extracted again with ethyl ether. The combined organic portions were washed once with water, once with saturated sodium chloride solution, dried over magnesium sulfate and filtered. The ether was distilled carefully until about 10 ml solution remained. The remainder was removed by rotary evaporation to give the volatile-ester as a yellow-orange liquid. This material was purified by distillation (Kujelrohr, b.p. 110°-120°, 35 mm) to obtain a clear oil.

IR(film): 1720, 1638 $cm^1$.

$^1$H NMR (CDCl$_3$): Partial, 6.66 (q, J=7 Hz, 1H); 3.70 (s, 3H); 2.55 (m, 1H); 1.80 (d, J=7 Hz, 1H).

$^{13}$C NMR (CDCl$_3$): 168.5, 138.1, 135.7, 51.1, 38.0, 30.3, 26.9, 26.6, 26.1, 25.9, 13.9.

Calculated for $C_{11}H_{18}O_2$: 182.1307, obtained (EI+): 182.1311.

2-Cyclohexyl-2-propen-1-ol

To a stirred solution of methyl 2-cyclohexyl-2-propenoate (2.0 g., 11.0 mmol) in 200 mi ethyl ether at −60° under argon was added diisobutylaluminum hydride (22 ml 1M solution in toluene). The solution was stirred for 0.5 hour, quenched with 3 ml isopropanol and warmed to room temperature. To this solution was added 25 ml water, and a white suspension formed. The mixture was filtered through celite, and the ether layer was washed twice with water, once with sodium chloride solution, dried over magnesium sulfate, filtered and concentrated to give a yellow liquid. This material was purified by flash chromatography (20% ethyl acetate/hexane) to give the alcohol as a clear liquid.

IR(CHCl$_3$): 3610 $cm^{-1}$.

$^1$H NMR (CDCl$_3$): 5.5 (q. J=6.1 Hz, 1H); 4.1 (s, 2H); 2.48 (m, 1H); 1.67 (d, J=6.6 Hz, 3H); 1.6-1.8 (m, 5H); 1.2-1.5 (m, 5H).

$^{13}$C NMR (CDCl$_3$): 144.3, 120.8, 65.2, 38.6, 32.6, 31.4, 26.9, 26.3, 26.2. 12.7.

Calculated for $C_{10}H_{18}O$: 154.1358, obtained (EI+): 154.1351.

2-Cyclohexyl-2-propenal

To a stirred suspension of pyridinium chlorochromate (3.2 g., 14.9 mmol) in 150 ml methylene chloride at room temperature under argon was added dropwise 2-cyclohexyl-2-propenal (1.15 g., 7.47 mmol) in 25 ml methylene chloride. After 0.5 hour the dark slurry was poured into 200 ml ethyl ether, stirred, and then filtered through florisil. The volatile solvents were distilled at atmospheric pressure, and the residue carefully concentrated by rotary evaporation. The volatile aldehyde was distilled (bp.=60°, 0.5 mm) to give a yellow liquid.

IR(CHCl$_3$): 1675, 1630 $cm^1$.

$^1$H NMR (CDCl$_3$): Partial, 9.32 (s, ]H); 6.48 (q, J=6.4 Hz, 1H); 2.58 (m, 1H); 2.02 (d, J=7.2 Hz, 3H).

$^{13}$C NMR (CDCl$_3$): 195.4, 150.1, 148.2. 36.4. 32.5. 29.7, 26.8, 26.7. 25.9, 14.9.

Calculated for $C_{10}H_{16}O$: 152.1201, obtained (EI+): 152.1198.

2-Cyclohexyl-1-trimethylsilyloxy-1,3-butadiene

To a stirred solution of 2-cyclohexyl-2-propenal (0.543 g., 3.6 mmol), zinc chloride (fused, catalytic amount), and triethylamine (1.3 ml, 9 mmol) in 2.6 ml anhydrous benzene at room temperature under argon was added trimethylsilylchloride (0.9 ml, 7.2 mmol). The mixture was stirred for 20 hrs during which time a precipitate formed. The suspension was then poured into a mixture of cold, saturated sodium bicarbonate and pentane. The combined organic portions were washed twice with cold, saturated sodium bicarbonate, once with cold, saturated sodium chloride, dried over magnesium sulfate and filtered. The volatile organic solvents were removed by atmospheric distillation, and the residue was then carefully concentrated by rotary evaporation to give the enol ether as a volatile, yellow liquid.

$^1$H NMR (CDCl$_3$): 6.32 (brs, 1H); 6.11 (dd, J=17 and 10 Hz, 1H); 5.09 (d, J=17 Hz, 1H); 4.79 (d, J=11 Hz, 1H); 2.45 (brt, 1H); 1.7 (m); 1.3 (m); 0.22 (s, 9H).

$^{13}$C NMR (CDCl$_3$): 139.7, 136.0, 127.2, 108.4, 36.0, 30.4, 27.2, 26.7, 26.4, 26.1, −0.6.

2-Cyclohexyl-5-hydroxy-5-r3-(2-trimethylsilylfuryl)]-2-pentenal

To a stirred solution of 5-trimethylsilyl-3-furaldehye (0.576 g., 3.4 mmol) in methylene chloride (10 ml) at −60° under argon was added dropwise boron trifloride etherate (0.44 ml, 3.6 mmol). After five minutes a solution of 2-cyclohexyl-1-trimethylsilyloxy-1,3-butadiene (0.764 g., 3.4 mmol) in 2 ml methylene chloride was added dropwise. The reaction mixture was stirred for 22 hours, quenched with saturated sodium bicarbonate, warmed to room temperature, and taken up in methylene chloride. The organic portion was washed once with saturated sodium bicarbonate solution, once with water, once with saturated sodium chloride solution, dried over magnesium sulfate, filtered and concentrated to give an orange oil. Purification by flash chromatography yielded the aldehyde as a yellow oil.

$^1$H NMR (CDCl$_3$): 9.32 (s, 1H); 7.61 (s, 1H); 7.66 (s, 1H); 6.44 (t, 1H); 4.88 (t, 1H); 2.85 (m, 2H); 2.5 (m, 1H); 1.7 (m); 1.4 (m), 0.28 (s, 9H).

$^{13}$C NMR (CDCl$_3$): 195.6, 162.0, 150.3, 148.7, 143.2, 128.1, 117.9, 65.9, 60.4, 37.3, 37.1, 29.8, 26.8, 25.8, 14.1, −1.8.

5-Cyclohexyl-3.6-dihydro-6-hydroxy-2-[3-(2-trimethylsilylfuryl)]-2H-pyran

2-Cyclohexyl-5-hydroxy-5-[3-(2-trimethylsilylfuryl)]-2-pentenal is dissolved in dry benzene (0.01M), placed in a quartz tube, flushed with oxygen free nitrogen for 0.5 to 1 hour, and irradiated at 254 nm for four hours. The solution is cooled and concentrated. The residue is purified by flash chromatography (ethyl acetate/ hexane) to give the desired acetal.

4-(5-Cyclohexyl-3.6-dihydro-6-hydroxy-2H-pyran-2-yl)-5-hydroxy-2(5H)-furanone A stirred solution of 5-cyclohexyl-3,6-dihydro-6-hydroxy-2-[3-(2-trimethyl-silylfuryl)]-2H-pyran and Rose Bengal (trace) is flushed with oxygen for 5 minutes and cooled to −78°. The solution is irradiated with a 150 to 300 W lamp, warmed to room temperature and concentrated to an oil. The residue is purified by flash chromatography (ethyl acetate/hexane or methylene chloride/ethyl acetate) to give the above titled furanone.

EXAMPLE 7

5-Hydroxy-5-[5-hydroxy-2(5H)-furanon-4-yl]-2-(3-phenyl propyl)-penten-2-al

A stirred solution of 5-(3-furyl)-5-hydroxy-2-(3-phenylpropyl)-2-pentenal (0.126 g., 0.444 mmol) prepared as in Example 1, and Rose Bengal (trace) in 100 ml methanol was flushed with oxygen and cooled to −78°. The pink solution was irradiated with a 200 W light bulb for two hours, warmed to room temperature, and concentrated to give a pink gum. This material was purified by flash chromatograpy (7:3 to 6:4 hexane/ethyl acetate) to give a regioisomeric mixture of two hydroxybutenolides. The mixture was separated by semi-preparative HPLC on a Whatman M-9 silica column, with an elution rate of 4 ml/min with 50% ethyl acetate/methylene chloride. The furanon-4-yl isomer was eluted at 22.5 minutes, followed by the furanon-3-yl isomer at 34 minutes. Concentration gave the purified compounds as clear oils.

Furanon-4-yl isomer

IR(CHCl$_3$): 3400 (broad), 1790 (sh), 1760, 1680 cm$^{-1}$.

$^1$H NMR (CDCl$_3$): 9.39 (s, 1H); 7.2 (m. 5H); 6.6 (m, 1H); 6.1 (m, 2H); 5.82 (brs, 1H); 4.75 (m, 1H); 3.5 (brs, 1H); 2.65 (m, 4H); 2.25 (m, 2H); 1.65 (m, 2H).

$^{13}$C NMR (as mixture of diasteriomers) (CDCl$_3$): 194.9, 170.4, 169.3, 148.1, 147.6, 146.1. 141.8, 128.4, 125.9, 118.7 and 118.5, 97.7 and 97.4, 67.0 and 66.7, 35.7, 34.5 and 34.2, 30.0, 23.8.

m/z Calculated for C$_{18}$H$_{16}$O$_3$ (M+-2 H$_2$O): 280.1099, obtained (EI+): 280.1098.

Furanon-3-yl isomer

IR(CHCl$_3$): 3400 (broad), 1765, 1680 cm$^{-1}$.

$^1$H NMR (CDCl$_3$): 9.38 (s, 1H); 7.2 (m, 5H); 7.09 (m, 1H); 6.57 (t, 1H); 6.14 (brs, 1H); 5.2 (brm, 1H); 4.69 (brs, 1H); 2.6 (m, 4H); 2.25 (m, 2H); 1.65 (m, 2H).

m/z Calculated for C$_{18}$H$_{18}$O$_4$ (M+-H$_2$O): 298.1205, obtained (EI+): 298.1207.

EXAMPLE 8

5-Acetoxy-5-(3-furyl)-2-(3-phenylpropyl)-2-pentenal

A solution of 5-(3-furyl)-5-hydroxy-2-(3-phenylpropyl)-2-pentenal (0.412 g., 1.45 mmol), acetic anhydride (0.3 ml), and pyridine (4 ml) was stirred at room temperature under argon for six hours, then allowed to stand at 0° for fifteen hours. The mixture was partitioned between ethyl ether and water, and the aqueous portion was separated and extracted again with ethyl ether. The combined organic portions were washed four times with 10% cupric sulfate, once with water, once with saturated sodium bicarbonate, once again with water, once with saturated sodium chloride, dried over magnesium sulfate, filtered and concentrated to give an orange oil. This material was purified by flash chromatography (9:1 to 8:2 hexane/ethyl acetate) to give the acetate as a yellow oil.

IR(film): 1740, 1685 cm$^1$.

$^1$H NMR (CDCl$_3$): 9.33 (s, 1H); 7.38 (d, J=8.1 Hz, 1H); 7.36 (d, J=2.3 Hz, 1H); 7.2 (m, 5H); 6.36 (m, 1H); 6.35 (s, 1H); 5.91 (t, J=6.5 Hz, 1H); 2.8 (m, 2H); 2.60 (t, 2H); 2.27 (t, 2H); 2.02 (s, 3H); 1.64 (p, 2H).

$^{13}$C NMR (CDCl$_3$): 194.3, 169.8, 147.8, 145.3, 143.3, 141.6, 140.1, 128.1, 125.6, 123.7, 108.4, 66.7, 35.5, 33.9, 29.8, 23.6, 20.8.

5-Acetoxy-[5-hydroxy-2(5H)-furanon-4-yl]-2-(3-phenylpropyl)-penten-2-al and

5-Acetoxy-[5-hydroxy-2(5H)-furanon-3-yl]-2-(3-phenylpropyl)-penten-2-al

A stirred solution of 5-acetoxy-5-(3-furyl)-2-(3-phenylpropyl)-2-pentenal (0.026 g., 0.080 mmol) and Rose Bengal (trace) in 10 ml methanol was flushed with oxygen and cooled to −78°. The pink solution was irradiated with a 200 H light bulb for one hour, warmed to room temperature, and concentrated to give a pink gum. This material was purified by flash chromatography (9:1 to 8:2 methylene chloride/ethyl acetate) to give a regioisomeric mixture of two hydroxybutenolides as an orangish glass. The mixture was separated by semi-preparative HPLC on a Whatman M-9 silica column, with an elution rate of 4 ml/min with 7:3 methylene chloride/ethyl acetate. The above titled furanon-4-yl compound was eluted at 14 minutes, followed by the above titled furanon-3-yl compound at 18.5 minutes. Concentration gave the purified compounds as clear glasses.

Furanon-4-yl isomer

IR(CHCl$_3$): 3580, 3380 (broad), 1795 (shoulder), 1765, 1745, 1685 cm$^{-1}$.

$^1$H NMR (mixture of diasteriomers) (CDCl$_3$): 9.39 (s, 1H); 7.22 (m, 5H); 6.4 (m, 1H); 6.19 (s, 0.5H); 6.01 (s, 1H); 5.95 (s, 0.5H); 5.65 (m, 1H); 2.8 (m, 2H); 2.63 (t, 2H); 2.29 (m, 2H); 2.12 and 2.09 (2s, 3H); 1.67 (m, 2H).

$^{13}$C NMR (mixture of diasteriomers) (CDCl$_3$): 194.6 and 194.3, 170.3 and 170.0, 169.6 and 169.3, 164.8, 146.6, 146.4 and 146.3, 145.4, 141.7 and 141.6, 128.4, 126.0 and 125.9, 119.9 and 119.5, 97.7 and 97.4, 68.1 and 67.8, 35.7 and 35.6, 32.0, 30.0, 23.7, 20.7.

m/z Calculated for C$_{20}$H$_{23}$O$_6$: 359.1495, obtained (CI+): 359.1489.

Furanon-3-yl isomer

IR(CHCl$_3$): 3580, 3380 (broad), 1770, 1750, 1685 cm$^{-1}$.

$^1$H NMR (mixture of diasteriomers) (CDCl$_1$): 9.36 (s, 1H); 7.2 (m, 5H); 7.02 (d, J=5.4 Hz, 1H); 6.40 (dd, J=7.5 and 14.7 Hz, 1H); 6.13 (m, ]H); 5.73 (m, 1H); 5.1 (brs, 1H); 2.87 (m, 2H); 2.61 (t, 2H); 2.28 (t, 2H); 2.10 and 2.09 (2s, 3H); 1.64 (m, 2H).

$^{13}$C NMR (mixture of diasteriomers) (CDCl$_3$): 194.8 and 194.7, 170.0 and 169.8, 168.9 and 168.8, 146.9, 146.7, 146.2 and 146.1, 145.8, 141.7, 135.8 and 135.7, 128.3, 125.8, 97.1 and 96.8, 67.3 and 67.0, 35.7, 32.0 and 31.7, 30.1, 23.8, 20.8.

m/z Calculated for C$_{20}$H$_{33}$O$_6$: 359.1495, obtained (CI+): 359.1495.

EXAMPLE 9

Using 5-(2-naphthyl)-1-bromopentane in place of 6-(benzo[b]-thien-2-yl)-1-bromohexane in the procedure of Example 4 gives 4-[5-(5-(2-naphthyl)pentyl)-3,6-dihydro-6-hydroxy-2H-pyran-2-yl]-5-hydroxy-2(5H)-furanone.

EXAMPLE 10

In the procedure of Example 1, using 8-phenyloct-6-enyl bromide in place of phenylpropyl bromide, the following products are obtained:
4-[3,6-dihydro-6-hydroxy-5-(8-phenyloct-6-enyl)-2H-pyran-2-yl]-5-hydroxy-2(5H)-furanone and
3-[3,6-dihydro-6-hydroxy-5-(8-phenyloct-6-enyl)-2H-pyran-2-yl]-5-hydroxy-2(5H)-furanone.

EXAMPLE 11

Using 1-bromododecane in place of 6-(benzo[b]thien-2-yl)-1-bromohexane in the procedure of example 4 gives 4-(5-dodecyl-3,6-dihydro-6-hydroxy-2H-pyran-2-yl)-5-hydroxy-2(5H)-furanone.

EXAMPLE 12

Using 1-bromo-5-cyclohexylpentane in place of 6-(benzo-[b]-thien-2-yl)-1-bromohexane in the procedure of example 4 gives 4-[5-(5-cyclohexylpentyl)-3,6-dihydro-6-hydroxy-2H-pyran-2-yl]-5-hydroxy-2(5H)-furanone.

The following test procedures may be used to demonstrate activity of compounds of this invention:

Inhibition of Phospholipase $A_2$

The effect of compounds of this invention on bee venom phospholipase $A_2$ is determined by the following procedure:

a. Bee venom phospholipase $A_2$ in 10 μM HEPES (pH 7.4) with 1 mM $CaCl_2$ is incubated with vehicle or test agent for 1.0 hour at 41°.
b. 1.36 mM phosphotidylcholine, 2.76 Mm Triton X-100 are dispersed in buffer by sonication and then mixed with L-3 phosphatidylcholine, 1-palmitoyl-2-(1-$^{14}$C) palmitoyl for 10 min.
C. Start the reaction by the addition of enzyme (0.495 units/ml).
d. Incubation for 15 sec. at 41°.
e. Reaction is terminated by addition of 2.5 ml of isopropanol: n-heptane: 0.5M $H_2SO_4$ (40:10:1 ; v:v:v).
f. 2.0 ml n-heptane and 1.0 ml $H_2O$ added; mixture centrifuged.
g. 2.0 ml n-heptane removed and treated with 200–300 mg of silica gel HR60.
h. Samples centrifuged; 1 ml of n-heptane SN removed and added to 10 ml scintillation fluid.
i. Samples counted on a scintillation counter.

Mouse Ear Anti-Inflammatory Assay

Test compound and phorbol myristate acetate (PMA) are topically applied simultaneously to the pinnae of the left ears of mice. PMA alone is applied to the right ear. Three hours and 20 minutes after application, the mice are sacrificed, left and right ears removed, and standard sized bores taken. Edema (inflammation) is measured as the difference in weight between left and right ears [Van Arman, C. G., *Clin Pharmacol Ther* (1974) 16:900–904].

Inhibition of Ornithine Decarboxylase (ODC)

Tape-stripping mouse epidermis and TPA are quick and convenient methods of inducing ODC activity. M. Connor and N. Lowe (*Cancer Res.* 43, 5174, 1983: *Brit. J. Dermatol.* 275, 98, 1984) have studied the ability of retinoids to inhibit ODC. Trans-retinoic acid, 13-cis retinoic acid, and etretinate were all active at inhibiting ODC and therapeutically active in humans. Therefore, inhibition of ODC is an in vivo method to demonstrate the potential efficacy of drugs for epidermal hyperproliferation such as psoriasis. Lowe e. al. (*J. Amer. Acad. Dermatol.* 6:697, 1982) have shown that polyamines and ODC are elevated in psoriasis.

In vitro methods have also been useful in determining the anti-hyperproliferative activity of drugs. C. Marcelo and J. Tomick (*J. Invest. Dermatol.* 81, 64s, 1983) have shown that neonatal mouse keratinocyte cultures can be used to identify drugs that inhibit DNA synthesis. More recently, R. Weiss, Eichner, R. and Sunn, T. T, *J Cell Biol.*, 98:1397–1406 (1984) have shown that epidermal cultures are in fact, a model of epidermal hyperproliferation and therefore a good model for testing drugs that inhibit hyperproliferation.

Calcium Channel (mobilization) inhibition assay

Polymorphonuclear leukocytes (PMNa), gastric glands, $GH_3$ cells, A431 cells, spleen cells, human keratinocytes corneal cells, etc. were loaded with the $Ca^{2+}$ sensitive fluorescent dye, Fura-2. The appropriate cell type was chosen and the potency and efficacy of the anti-inflammatory furanones on calcium mobilization, calcium channel inhibition quantitated. The methods used for A431 cells listed below are representative of those used for other cells.

A431 cells were detached using a 5-10 min trypsin-EDTA treatment whereas $GH_3$ cells were treated 2 to 5 min with a 1% pancreatin solution. Cells were immediately washed twice in a 20mM HEPES buffer (pH 7.4) containing 120mm NaCl, 6 Mm KCl, 1 mM $MgSO_4$, 1 mg/ml glucose and 1 mg/ml pyruvate and 1.4mm calcium (medium A). Approximately $5\times10$ cells were suspended in medium A and incubated with 4 μM fura-2-AM for 15 min at 37° C. After washing the fura-2 loaded cells, the uptake of dye was checked using fluorescence microscopy and found to be evenly distributed in the cytosol of all cells. Fluorescence was continuously recorded with a Perkin-Elmer LS-5 spectrofluorometer. The excitation wavelength was set at 340 nm and emission wavelength set at 500 nm. The cell suspension was continually stirred, maintained at 37° C. and equilibrated for approximately 5 min before addition of various agents. $[Ca^{2+}]_i$ was calculated using the following formula:

$$[Ca^{2+}]_i = 220 \frac{F - F_{min}}{F_{max} - F}$$

All fluorescence values were measured relative to a EGTA-quenched signal determined as follows: F was the relative fluorescence measurement of the sample. $F_{max}$ was determined by lysing the cells with digitonin (100 μg/ml) in DMSO. After $F_{max}$ was determined the pH was adjusted to 8, with NaOH and $Ca^{3+}$ chelated with 3mM EGTA to totally quench the fura-2 signal and obtain $F_{min}$.

When quin-2 was used, cells were incubated with 10 μM quin-2 at 37° C. for 1 hr, washed and then used.

What is claimed is:

1. A compound of the formula:

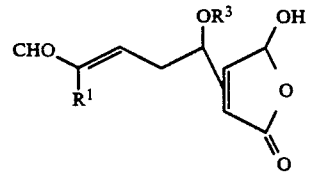

in which:

$R_1$ is phenyl ($C_1$–$C_{17}$ alkyl or alkenyl having 1-5 unconjugated double bonds), benzothienyl ($C_1$–$C_{17}$ alkyl or alkenyl having 1-5 unconjugated double bonds), or naphthyl ($C_1$–$C_{17}$ alkyl or alkenyl having 1-5 unconjugated double bonds); and
$R_3$ is hydrogen or $C_1$–$C_4$ alkanoyl.

2. A compound of claim 1 in which $R_1$ is phenyl ($C_1$–$C_{17}$ alkyl) or benzothienyl ($C_1$–$C_{17}$ alkyl) and $R_3$ is hydrogen or acetyl.

3. A pharmaceutical composition having anti-inflammatory activity in mammals which comprises a pharmaceutical carrier and a therapeutically effective amount of a compound of claim 1.

* * * * *

UNITED STATES PATENT AND TRADEMARK OFFICE
CERTIFICATE OF CORRECTION

PATENT NO. : 5,258,400
DATED : November 2, 1993
INVENTOR(S) : Michael E. Garst, et al.

It is certified that error appears in the above-identified patent and that said Letters Patent is hereby corrected as shown below:

Column 1, line 26, "immunosuppresive" should be —immunosuppressive—;
Column 4, line 39, "S" should be —5—;
Column 6, line 63, "-780" should be — -78°—;
Column 7, line 23, "780" should be —78°—;
Column 7, line 46, "$^{31}$C" should be —$^{13}$C—;
Column 7, line 51, "-,1,3-" should read -- -1,3- --.
Column 8, line 38, "i-n" should be —in—;
Column 8, line 49, "5H)," should be —5H);—;
Column 9, line 10, "cyranyl" should be —pyranyl—;
Column 9, line 29, "]H" should be —1H—;
Column 9, line 64, "-780" should be — -78°—;
Column 10, line 20 "$^{13}$ C" should be —$^{13}$C—;
Column 10, line 29, "1 7.2" should be —7.2—;
Column 10, line 65, "J.2H" should be —J=2H—;
Column 11, line 45, "3.6" should be —3,6—;
Column 11, line 45 "Pyran" should be —pyran—;
Column 11, line 65, "2-]6-" should be —2-[6- —;
Column 11, line 67, "00" should be —0 —;
Column 13, line 6, "60°" should read -- -60°--.
Column 13, line 29, "3.6" should be —3,6—;
Column 13, line 32, "2-(6-" should read --2-[6- --;
Column 13, line 56, "(b]" should be —[b]—;

UNITED STATES PATENT AND TRADEMARK OFFICE
CERTIFICATE OF CORRECTION

PATENT NO. : 5,258,400
DATED : November 2, 1993
INVENTOR(S) : Michael E. Garst

It is certified that error appears in the above-identified patent and that said Letters Patent is hereby corrected as shown below:

Column 13, line 68, "]H" should be —1H—;
Column 14, line 43, "26.8"." should be —26.8,—;
Column 14, line 64, "J.16" should be —J=16—;
Column 15, line 68, after "(CHCl$_3$)" insert —:—;
Column 16, line 31, "cm$^1$" should be —cm$^{-1}$—;
Column 16, line 44, "00" should be —0°—;
Column 17, line 7, "cm$^1$" should be —cm$^{-1}$—;
Column 17, line 17, "mi" should be —ml—;
Column 17, line 49, "cm $^1$" should be —cm$^{-1}$—;
Column 17, line 50, "]H" should be —1H—;
Column 18, line 12, "r3" should be —[3—;
Column 18, line 36, "3.6" should be —3,6—;
Column 18, line 47, "3.6" should be —3,6—;
Column 19, line 47, "cm$^1$" should be —cm$^{-1}$—;
Column 19, line 65, "H" should be — W—;
Column 20, line 31, "]H" should be —1H—;
Column 21, line 10, "A$_2$in" should be —A$_2$ in—;
Column 21, line 13, "Mm" should be —mM—;
Column 21, line 44, "1983:" should be —1983—;
Column 22, line 12, "120mm" should be —120mM—;
Column 22, line 12, "6Mm" should be —6mM—;

UNITED STATES PATENT AND TRADEMARK OFFICE
CERTIFICATE OF CORRECTION

PATENT NO. : 5,258,400

DATED : November 2, 1993

INVENTOR(S) : Michael E. Garst

It is certified that error appears in the above-identified patent and that said Letters Patent is hereby corrected as shown below:

Column 22, line 13, "1.4mm" should be —1.4mM—;

Column 22, line 14, "5x10" should be —$5 \times 10^6$—;

Column 22, line 36, "$Ca^{3+}$" should be —$Ca^{2+}$—.

Signed and Sealed this

Twenty-sixth Day of July, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,258,400
DATED : November 2, 1993
INVENTOR(S) : Michael E. Garst, et al.

It is certified that error appears in the above-identified patent and that said Letters Patent is hereby corrected as shown below:

Column 16, line 11, "hydroxypropionate" should be —butanoate—;
Column 16, line 39, "propenoate" should be —butenoate—;
Column 16, line 42, "hydroxypropionate" should be —hydroxybutanoate—;
Column 17, line 15, "propen-1-ol" should be —buten-1-ol—;
Column 17, line 17, "propenoate" should be —butenoate—;
Column 17, line 37, "propenal" should be —butenal—;
Column 17, line 42, "propenal" should be —buten-1-ol—;
Column 21, line 51, "e. al." should be —et al.—.

Signed and Sealed this

Fourth Day of October, 1994

Attest:

BRUCE LEHMAN

*Attesting Officer*  *Commissioner of Patents and Trademarks*